United States Patent
Koga et al.

(10) Patent No.: US 8,106,206 B2
(45) Date of Patent: Jan. 31, 2012

(54) SOLID LUMINESCENT QUINOLINE COMPOUNDS

(75) Inventors: Noboru Koga, Fukuoka (JP); Satoru Karasawa, Fukuoka (JP); Yuichiro Abe, Fukuoka (JP)

(73) Assignee: Kyushu University, National University Corporation, Fukuoka-shi (JP)

( * ) Notice: Subject to any disclaimer, the term of this patent is extended or adjusted under 35 U.S.C. 154(b) by 0 days.

(21) Appl. No.: 12/950,261

(22) Filed: Nov. 19, 2010

(65) Prior Publication Data

US 2011/0263861 A1    Oct. 27, 2011

Related U.S. Application Data

(60) Provisional application No. 61/262,625, filed on Nov. 19, 2009.

(51) Int. Cl.
| | |
|---|---|
| C07D 401/00 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |
| C07D 421/00 | (2006.01) |
| C07D 215/38 | (2006.01) |
| C07D 215/18 | (2006.01) |
| C07D 213/26 | (2006.01) |

(52) U.S. Cl. ..... 546/167; 546/171; 546/180; 546/276.4; 546/346

(58) Field of Classification Search .................. None
See application file for complete search history.

(56) References Cited

U.S. PATENT DOCUMENTS 4,804,404 A * 2/1989 Hagen et al. .................. 504/247

FOREIGN PATENT DOCUMENTS

JP   11-279152 A   * 12/1999
JP   2008-115105 A * 5/2008

OTHER PUBLICATIONS

Hopkins, TA. et al. Substituted Aluminum and Zinc Quinolates with Blue-Shifted Absorbance/Luminescence Bands: Synthesis and Spectroscopic, Photoluminescence, and Electroluminescence Characterization. Chem. Mater. 1996, vol. 8, p. 344-345, introduction.*
Chi, KW. et al. Reaction of perfluoro-2-methylpent-2-ene and perfluoro-5-azanon-4-ene with aniline and its derivatives. J. Fluorine Chem. 2000, vol. 104, p. 263.*

* cited by examiner

Primary Examiner — Rita Desai
Assistant Examiner — Ben Michelson
(74) Attorney, Agent, or Firm — Edwards Wildman Palmer LLP

(57) ABSTRACT

Provided is a solid luminescent quinoline compound capable of emitting light in a crystalline state, capable of changing the luminescent color not requiring modification of molecular configuration and capable of emitting light in response to external pressure such as heat, physical pressure, etc. The quinoline compound is represented by the following general formula (1):

[Formula 1]

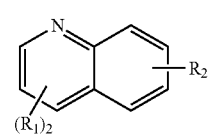

(1)

wherein $R_1$ may be the same or different, each representing any of $CF_3$ or $CF_3CF_2$; $R_2$ represents any of an amino group, an N,N-dimethylamino group, an N-phenylamino group, a carbazole group, an N-methylamino group or an N-methyl-N-phenylamino group.

7 Claims, 4 Drawing Sheets

Luminescence behavior of compound 4 in hexane solution (left), in chloroform solution (center) and in ethyl acetate solution (right) (as photographed under black light at 365 nm)

Emission spectra of compound 4 in hexane solution, in chloroform solution and in ethyl acetate solution Solid luminescence behavior of B-type (left) and G-type (right) of compound 4 (as photographed under black light at 365 nm)

Solution emission spectrum in hexane solution of compound 4, and solid emission spectra of B-type and G-type of compound 4

Luminescence behavior of compound 6 in hexane solution, in chloroform solution, in ethyl acetate solution and in dimethyl-sulfoxide solution (in that order from the left, as photographed under black light at 365 nm)

Solution-state emission spectra (right axis) and absorption spectra (left axis) of compound 6, the solvent shown above

Fig. 7

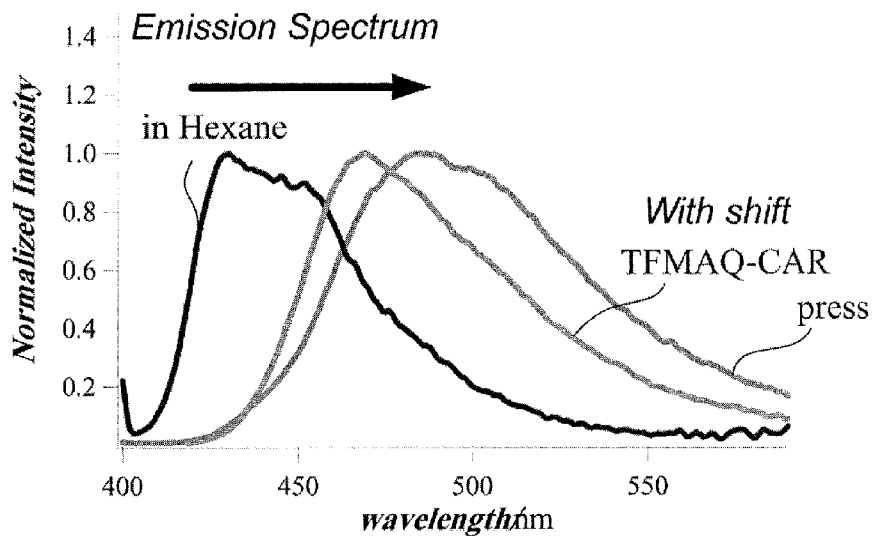

Emission spectra of crystal before and after pressure application in hexane solution of compound 6

Fig. 8

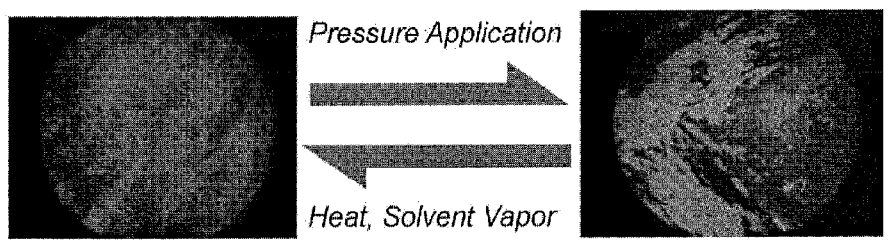

Luminescent behavior of crystal of compound 6 before pressure application (left) and after pressure application (right) (the pressure-given crystal is restored to its original state after exposed to heating or organic solvent) (as photographed under black light at 365 nm)

SOLID LUMINESCENT QUINOLINE COMPOUNDS

The present application claims priority to U.S. provisional application 61/262,625, filed Nov. 19, 2009, the entire description of which is herein incorporated by reference especially as disclosure.

FIELD OF THE INVENTION

The present invention relates to a novel, solid luminescent quinoline compound.

BACKGROUND ART

There exist many fluorescent organic compounds, which are used as luminescent materials or are used for detection of minor components, and for cellular imaging, bioimaging, etc. However, for example, as shown in Non-Patent Reference 1, already-existing luminescent compounds could emit light as simple molecules in a solution state, but there are extremely few cases of emitting light in a solid or crystalline state where molecules are densely associated and aggregated. The reason for this is considered that, as a result of intermolecular energy transfer through molecular aggregation, the photon yield would lower to extinction. This involves a problem in that device designing with a solid luminescent compound is limited. Another problem is that the means of changing the luminescent color is limited to modification of molecular configuration.

PRIOR ART REFERENCE

Non-Patent Reference

Non-Patent Reference 1: The Journal of Physical Chemistry, Vol. 105, 1097, 2001

SUMMARY OF THE INVENTION

Problem to be Solved by Invention

Accordingly, an object of the invention is to solve the above-mentioned, already-existing problems and to provide a solid luminescent quinoline compound capable of emitting light in a crystalline state, capable of changing the luminescent color not requiring modification of molecular configuration and capable of emitting light in response to external pressure such as heat and pressure.

Means for Solving Problem

The present inventors have assiduously studied for the purpose of solving the above-mentioned problems, and have obtained the following findings.

Specifically, for obtaining a compound capable of emitting light in a solid state, the intermolecular steric structure of the compound must be controlled. The inventors have found that, by introducing a bulky substituent, trifluoromethyl group into a quinoline ring of a compound, the extinction caused by the π-π stacking between the aromatic rings may be controlled and the compound can thereby emit light in a solid state. In addition, the trifluoromethyl group is an electron-attracting substituent, and when the group is introduced into a molecule along with an electron-donating group thereinto, then it can produce a large charge-separated state in an excited state owing to the push-pull effect of electrons. The inventors have confirmed excellent solvatochromism in a compound into which an amino group, an N,N-dimethylamino group, a phenylamino group or a carbazole group as an electron-donating group has been introduced according to this method. Changing the recrystallization solvent for a compound substituted with a phenylamino group gives crystal polymorphism of B-type and G-type. These are considered to have resulted from observation of a change in the wavelength of the emitted light due to the difference in the crystal structures. Further, there is observed piezochromism that changes the fluorescent wavelength with application of pressure to a compound having a carbazole group in a solid state. This phenomenon is peculiar to a solid luminescent substance, and it may be considered that the intermolecular alignment in the compound would be changed by application of pressure thereto, and the emitted light would be thereby changed.

The present invention has been made based on the above-mentioned findings, and the quinoline compound of the invention is represented by the following general formula (1):

[Formula 1]

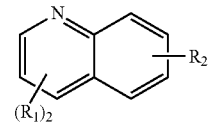

(1)

wherein $R_1$ may be the same or different, each representing any of $CF_3$ or $CF_3CF_2$; $R_2$ represents any of an amino group, an N,N-dimethylamino group, an N-phenylamino group, a carbazole group, an N-methylamino group or an N-methyl-N-phenylamino group.

The quinoline compound of the invention is represented by the following chemical formula (1-1):

[Formula 2]

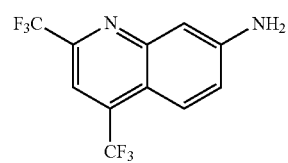

(1-1)

The quinoline compound of the invention is represented by the following chemical formula (1-2):

[Formula 3]

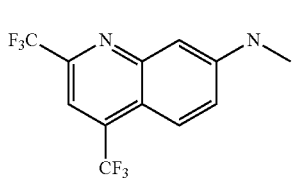

(1-2)

The quinoline compound of the invention is represented by the following chemical formula (1-3):

[Formula 4]

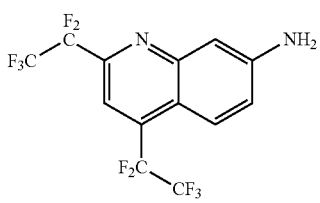

(1-3)

The quinoline compound of the invention is represented by the following chemical formula (1-4):

[Formula 5]

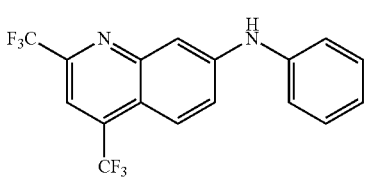

(1-4)

The quinoline compound of the invention is represented by the following chemical formula (1-5):

[Formula 6]

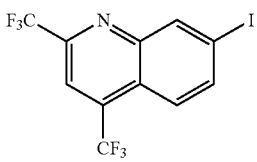

(1-5)

The quinoline compound of the invention is represented by the following chemical formula (1-6):

[Formula 7]

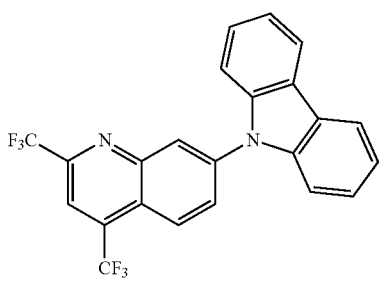

(1-6)

Effect of Invention

The quinoline compound of the invention has a bulky substituent, trifluoromethyl group or the like introduced into the quinoline ring thereof, and therefore can control the extinction to be caused by the n-n stacking between the aromatic rings and can thereby emit light in a solid state. In addition, the trifluoromethyl group or the like is an electron-attracting substituent, and when the group is introduced into a molecule along with an electron-donating group thereinto, then it can produce a large charge-separated state in an excited state owing to the push-pull effect of electrons. Accordingly, excellent solvatochromism can be realized in a compound into which an amino group, an N,N-dimethylamino group, an N-phenylamino group, a carbazole group, an N-methylamino group, an N-methyl-N-phenylamino group or the like is introduced as an electron-donating group. Changing the recrystallization solvent for a compound substituted with a phenylamino group gives crystal polymorphism of B-type and G-type, which can realize different color emission owing to the difference in the crystal structure between them. Further, the compound having a carbazole group emits colored light under pressure in a solid state, and can realize light emission in response to external pressure.

BRIEF DESCRIPTION OF THE DRAWINGS

FIG. 7 shows the emission spectra of the crystal of the quinoline compound of the invention (compound 6) before pressure application and after pressure application in a hexane solution.

FIG. 8 shows the emission behavior of the crystal of the quinoline compound of the invention (compound 6) before pressure application and after pressure application.

DESCRIPTION OF THE PREFERRED EMBODIMENTS

Figure 1:
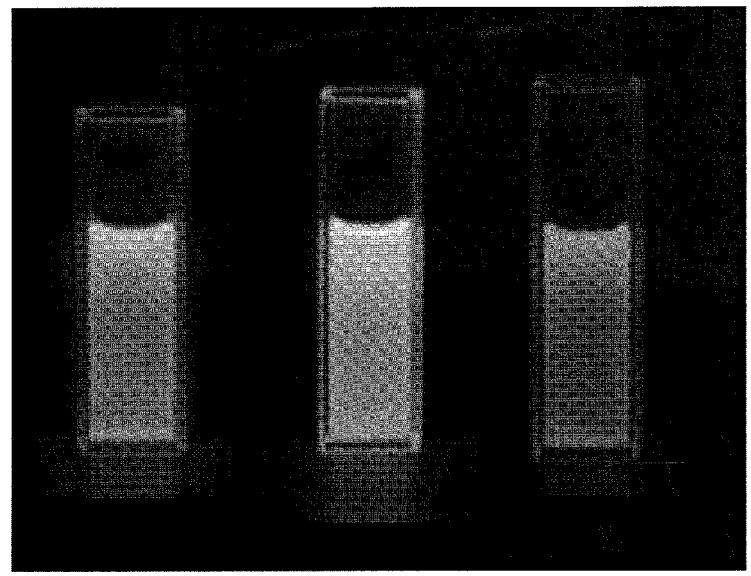
FIG. 1 shows the luminescence behavior of a quinoline compound of the invention (compound 4) in a hexane solution, a chloroform solution and an ethyl acetate solution.

Embodiments of the invention are described concretely hereinunder with reference to Examples; however, the invention is not limited to these Examples.

The quinoline compound of the invention is represented by the following general formula (1):

[Formula 8]

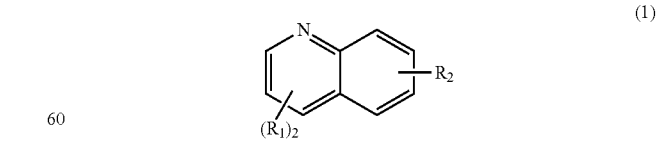

(1)

wherein $R_1$ may be the same or different, each representing any of $CF_3$ or $CF_3CF_2$; $R_2$ represents any of an amino group, an N,N-dimethylamino group, an N-phenylamino group, a carbazole group, an N-methylamino group or an N-methyl-N-phenylamino group.

$R_1$ may be any of an alkyl chain represented by $C_nH_{2n+1}$ where n is from 0 to 10, an alkyl chain represented by $C_nF_{2n}+1$ where n is from 0 to 10, a nitro group, a urea group, an amide group, a chlorine group, a bromine group or an iodine group, but is preferably $CF_3$ or $CF_3CF_2$.

$R_2$ may be any of an amino group, an N,N-dimethylamino group, an N,N-diethylamino group, an N,N-dipropylamino group, an N,N-dibutylamino group, an N,N-dipentylamino group, an N,N-dihexylamino group, an N-phenylamino group, a carbazole group, an N-methylamino group, an N-ethylamino group, an N-propylamino group, an N-butylamino group, an N-pentaneamino group, an N-hexylamino group, an N-phenylamino group or an N-methyl-N-phenylamino group, but is preferably an amino group, an N,N-dimethylamino group, an N-phenylamino group, a carbazole group, an N-methylamino group or an N-methyl-N-phenylamino group.

The quinoline compound of the invention is represented by the above-mentioned general formula (1), and concretely, the compounds represented by the following chemical formulae (1-1) to (1-6) are preferred.

[Formula 9]

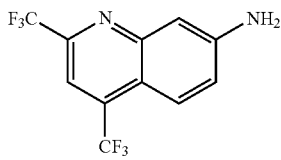
(1-1)

[Formula 3]

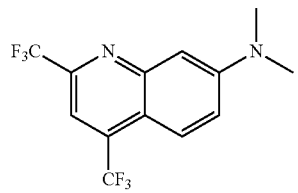
(1-2)

[Formula 4]

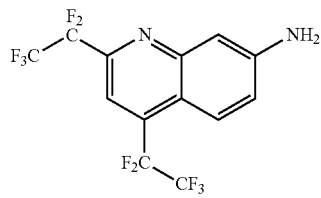
(1-3)

[Formula 5]

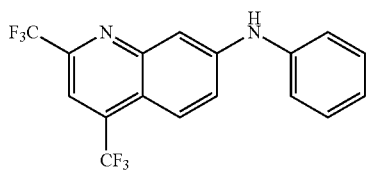
(1-4)

[Formula 6]

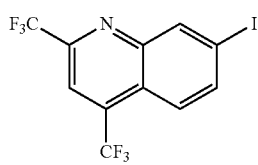
(1-5)

[Formula 7]

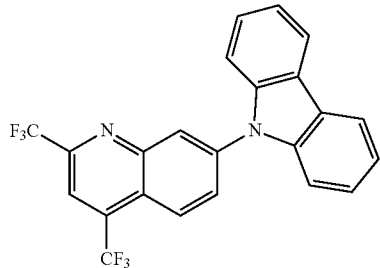
(1-6)

The production method for the quinoline compound of the invention is not specifically defined. For example, the compound is preferably produced according to the following production schemes:

Production Scheme 1:
[Formula 8]

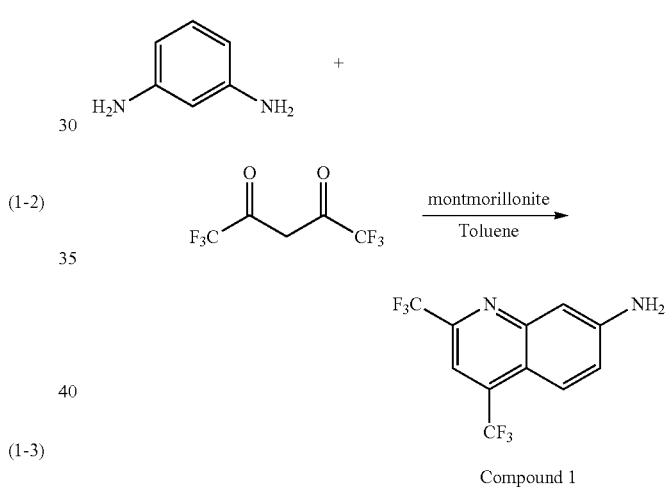

Compound 1

Production Scheme 2:
[Formula 9]

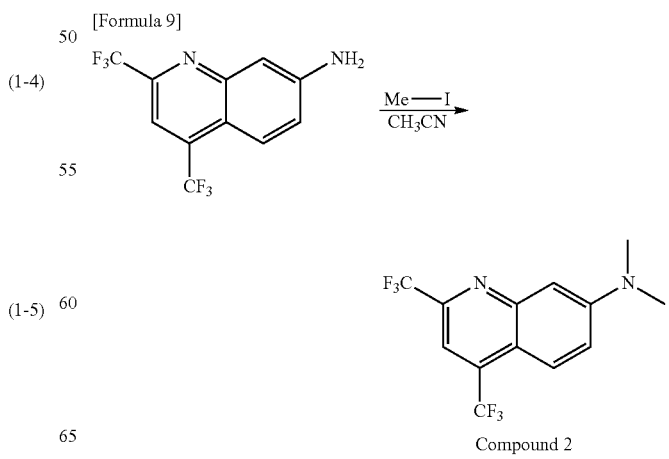

Compound 2

Production Scheme 3:
[Formula 10]

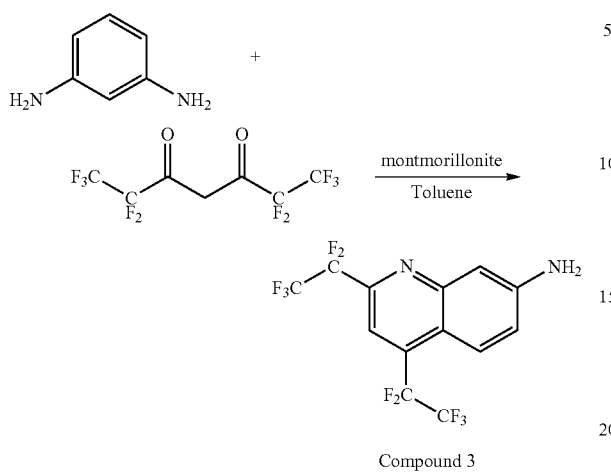

Compound 3

Production Scheme 4:
[Formula 11]

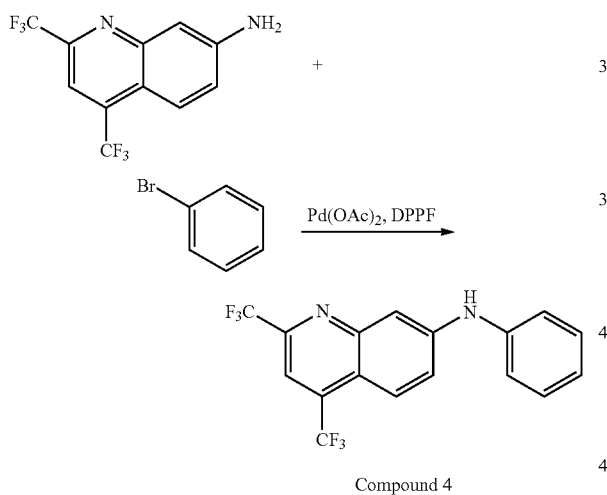

Compound 4

Production Scheme 5:
[Formula 12]

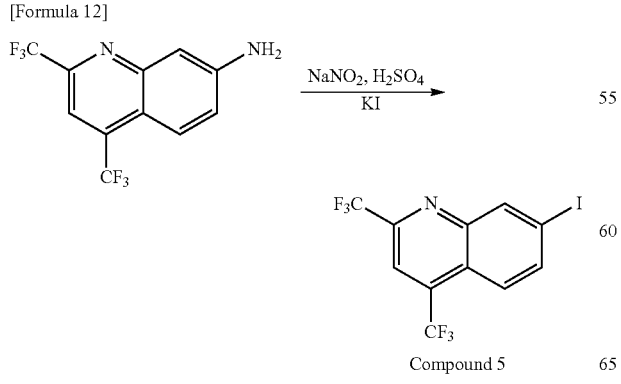

Compound 5

Production Scheme 6:
[Formula 13]

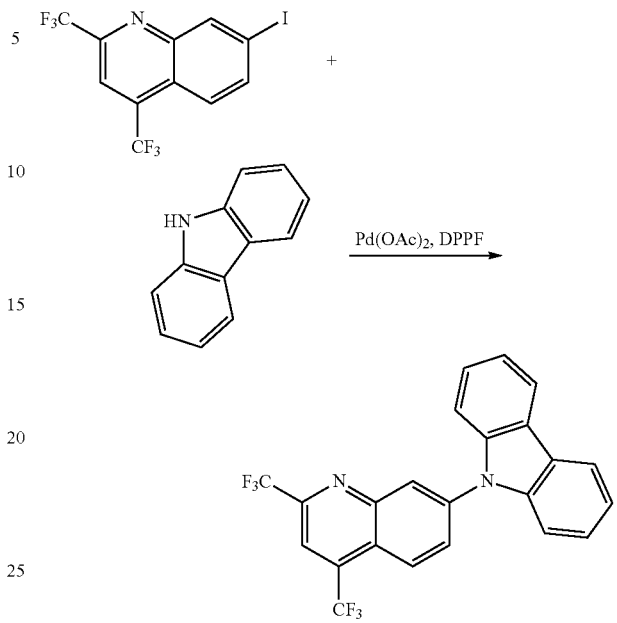

Compound 6

EXAMPLES

Concrete compounds are described below with reference to their production methods.

Example 1

Compound 1: 2,4-trifluoromethyl-7-aminoquinoline, TFMAQ

According to the above-mentioned production scheme 1, 2,4-trifluoromethyl-7-aminoquinoline (TFMAQ) was produced.

1.0 g (9.26 mmol) of m-phenylenediamine and 1.5 g of montmorillonite were put into 30 ml of toluene, and dissolved therein under heat. 1.6 ml (1.1 eq) of haxafluoroacetylacetone was added thereto and heated at 90° C., and after 1 hour, the heating was stopped, and after hot suction filtration (washing with ethyl acetate), the solvent was evaporated away under reduced pressure to around a half. A yellow solid precipitated by cooling was suction-filtered and washed with hexane to be 2.5 g (96%) of a yellow solid.

Subsequently this was recrystallized to be a yellow crystal of the compound 1.

[Formula 2]

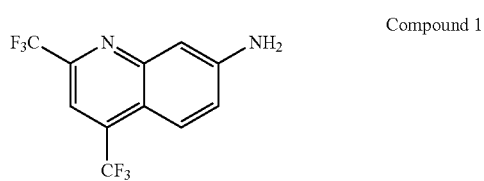

Compound 1

¹H-NMR (270 MHz, CDCl₃)
δ=8.00 (d, 1H, J=8.72 Hz)
7.71 (s, 1H)
7.37 (d, 1H, J=2.03 Hz)
7.21 (d, 1H, J=9.40 Hz)
4.34 (s, 2H)
FAB-MASS
281 (M+1)
IR (KBr)
3461, 3333 cm⁻¹
Elementary Analysis
Calc. C, 47.16; H, 2.16; N, 10.00
Found. C, 47.33; H, 2.13; N, 9.87

Example 2

Compound 2:
2,4-trifluoromethyl-7-N,N-dimethylaminoquinoline

According to the above-mentioned production scheme 2, 2,4-trifluoromethyl-7-N,N-dimethylaminoquinoline was produced.

280 mg (1.0 mmol) of TFMAQ was dissolved in 7 ml of acetonitrile. 0.5 ml (8 eq) of methyl iodide was added to the solution, and heated at 90° C. After thus heated for 14 hours, 0.5 ml (8 eq) of methyl iodide was further added thereto, heated for 2 hours, then the reaction was stopped, the solvent was evaporated away under reduced pressure, and the residue was purified through silica gel column chromatography (eluted with hexane:ethyl acetate=10:1) to give 50 mg (yield, 16%) of the compound 2 as an orange solid.

[Formula 3]

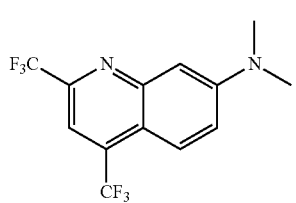

Compound 2

¹H-NMR (270 MHz, CDCl₃)
δ=8.02 (dd, 1H, J=7.4 Hz)
7.64 (s, 1H)
7.38 (dd, 1H, J=6.8 Hz)
7.29 (d, 1H, J=3.5 Hz)
3.17 (s, 6H)

Example 3

Compound 3: 2,3-pentafluoroethyl-7-aminoquinoline

According to the above-mentioned production scheme 3, 2,3-pentafluoroethyl-7-aminoquinoline was produced.

200 mg (1.85 mmol) of m-phenylenediamine and 0.56 g of montmorillonite were dissolved in 16 ml of chloroform. 0.6 ml (1.1 eq) of decafluoroheptane-3,5-dione was added thereto and heated at 70° C. After this was heated for 17 hours in total, 0.6 ml (1.1 eq) of decafluoroheptane-3,5-dione was further added thereto. After 8 hours, the heating was stopped, and after suction filtration, the solvent was evaporated away under reduced pressure, and the residue was purified through silica gel column chromatography (eluted with chloroform) to give 557 mg (79%) of the compound 3 as a yellow solid.

[Formula 4]

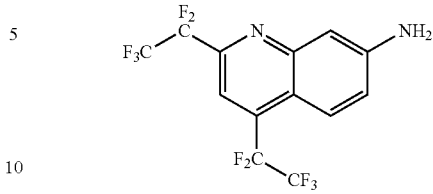

Compound 3

¹H-NMR (270 MHz, CDCl₃)
δ=8.05 (d, 1H, J=10.1 Hz)
7.67 (s, 1H)
7.38 (d, 1H, J=2.70 Hz)
7.19 (d, 1H, J=9.45 Hz)
4.33 (s, 2H)
FAB-MASS
380 (M⁺)

Example 4

Compound 4:
2,4-trifluoromethyl-7-N-phenylaminoquinoline

According to the above-mentioned production scheme 4, 2,4-trifluoromethyl-7-N-phenylaminoquinoline was produced.

1.0 g (3.6 mmol) of the compound 1 (TFMAQ), 200 mg (0.1 eq) of 1,1'-bis(diphenylphosphino)ferrocene (DPPF) and 400 mg (1.0 eq) of potassium tert-butoxide and toluene were added, and then processed for bubbling with N₂ and for freezing followed by thawing three times each so as to create a nitrogen atmosphere. 40 mg (0.05 eq) of palladium(II) acetate and 0.37 ml (1.0 eq) of bromobenzene were added thereto and heated at 100° C. still in the nitrogen atmosphere. After 6 hours, the heating was stopped, and water was added to stop the reaction. This was extracted with ethyl acetate, the organic layer was dried with magnesium sulfate, and the solvent was evaporated away under reduced pressure. The residue was purified through silica gel column chromatography (hexane: ethyl acetate=100:1) to give 630 mg (49%) of a pale yellow solid. This was recrystallized from a mixed solvent of ether: hexane (=10:3 by volume) to give a green-emitting crystal (G-type). On the other hand, the solid was recrystallized from ether:hexane (=1:10) to give a blue-emitting crystal (B-type).

[Formula 5]

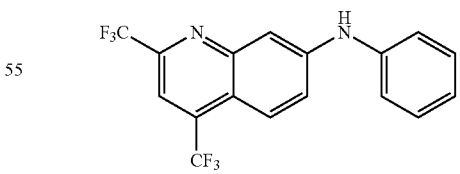

Compound 4

¹H-NMR (270 MHz, CDCl₃)
δ=8.06 (dd, 1H, J=9.45 Hz)
7.75 (s, 1H)
7.73 (d, 1H, J=2.70 Hz)
7.47 (dd, 1H, J=2.70 Hz)
7.41 (t, 2H), 7.41 (t, 2H)
7.18 (t, 1H)

Elementary Analysis:
Calc. C, 57.31; H, 2.83; N, 7.86
Found. C, 57.31; H, 2.85; N, 7.92
The melting point of G-type and B-type was measured to be as follows:
Melting Point Measurement (° C.)
G-type: 119 to 125, B-type: 118 to 122

Example 5

Compound 5: 2,4-trifluoromethyl-7-iodoquinoline

According to the above-mentioned production scheme 5, 2,4-trifluoromethyl-7-iodoquinoline was produced.

2.0 g (7.1 mmol) of the compound 1 (TFMAQ) was dissolved in an aqueous sulfuric acid solution of 5 ml of water and 30 ml of concentrated sulfuric acid with adding ice thereto. While the solution was kept at a temperature not higher than 5° C., an aqueous solution of 980 mg (2 eq) of sodium nitride was gradually and dropwise added thereto. After complete addition, this was stirred for 10 minutes, and then an aqueous solution of 3.45 g (3 eq) of potassium iodide was added thereto. Subsequently, this was stirred for 10 minutes, and heated at 80° C. for 15 minutes. The resulting solid was washed with an aqueous sodium sulfite solution, and collected through filtration under suction. This was dried in vacuum to give 2.40 g (86%) of a brown solid.

[Formula 6]

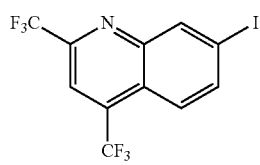

Compound 5

$^1$H-NMR (270 MHz, CDCl$_3$)
δ=8.80 (s, 1H)
8.08 (d, 1H, J=7.37 Hz)
8.03 (s, 1H)
7.92 (d, 1H, J=10.8 Hz)
FAB-MASS
392 (M+1)

Example 6

Compound 6: 2,4-trifluoromethyl-7-carbazoylquinoline

According to the above-mentioned production scheme 6, 2,4-trifluoromethyl-7-carbazoylquinoline was produced.

150 mg (0.39 mmol) of the compound 5,2,4-trifluoromethyl-7-iodoquinoline, 21.3 mg (0.1 eq) of DPPF, 96.5 mg (1.5 eq) of carbazole, 70 mg (1.6 eq) of potassium tert-butoxide and 8 ml of toluene were added, and then processed for bubbling with N$_2$ and for freezing followed by thawing so as to create a nitrogen atmosphere. 4.4 mg (0.05 eq) of palladium (II) acetate was added thereto and heated at 100° C. still in the nitrogen atmosphere. After 4 hours of heating, water was added to stop the reaction. This was extracted with ethyl acetate, dried with magnesium sulfate, and purified through silica gel column chromatography (eluted with hexane:ethyl acetate=100:1) to give 93 mg (yield, 56%) of the compound 6 as a pale yellow solid.

[Formula 7]

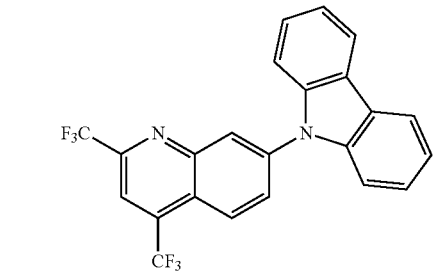

Compound 6

$^1$H-NMR (270 MHz, CDCl$_3$)
δ=8.06 (dd, 1H, J=9.45 Hz)
7.75 (s, 1H)
7.73 (d, 1H, J=2.70 Hz)
7.47 (dd, 1H, J=2.70 Hz)
7.41 (t, 2H), 7.41 (t, 2H)
7.18 (t, 1H)
Elementary Analysis
Calc. C, 64.19; H, 2.81; N, 6.51
Found. C, 64.09; H, 2.81; N, 6.53

$^1$H-NMR was analyzed as follows: The compound was dissolved in heavy chloroform to give a solution having a controlled concentration of a few mM. A standard sample, tetramethylsilane was added to the solution, and this was analyzed with JEOL (Japan Electro Optical Laboratory)'s JMS-SX102.

FAB-MASS was analyzed as follows: M-nitrobenzyl alcohol was used as a matrix. The compound was analyzed with JEOL's JMS-SX102 in a positive mode.

IR (KBr) was analyzed as follows: The compound was mixed with potassium bromide, finely pounded in a mortar into fine particles, pelletized with a pelletizer into pellets. The pellet was analyzed with JASCO's 420FT-IR.

The elementary analysis was made by the Analytical Center of Faculty of Science in Kyushu University.

Next, the luminescence behavior of 2,4-trifluoromethyl-7-N-phenylaminoquinoline (compound 4) was investigated. A sample of the compound prepared to have a concentration of 10 μM was put into a cuvette of 1 cm×1 cm×2 cm, and analyzed in a hexane, chloroform and ethyl acetate solution, using Perkin Elmer's LS50B. The excitation wavelength was 390 nm.

The results are shown in Table 1 below. The emission spectra are shown in FIG. 1.

TABLE 1

|  | $\lambda_{max}$ (nm) | ε | $\lambda_{fmax}$ (nm) | Φ | τ (ns) |
|---|---|---|---|---|---|
| hexane | 392 |  | 446 | 0.33 | 13.7 |
| chloroform | 402 | 6450 | 504 | 0.21 | 9.38 |
| ethyl acetate | 410 |  | 541 | <0.03 | 0.88 |

Figure 2:
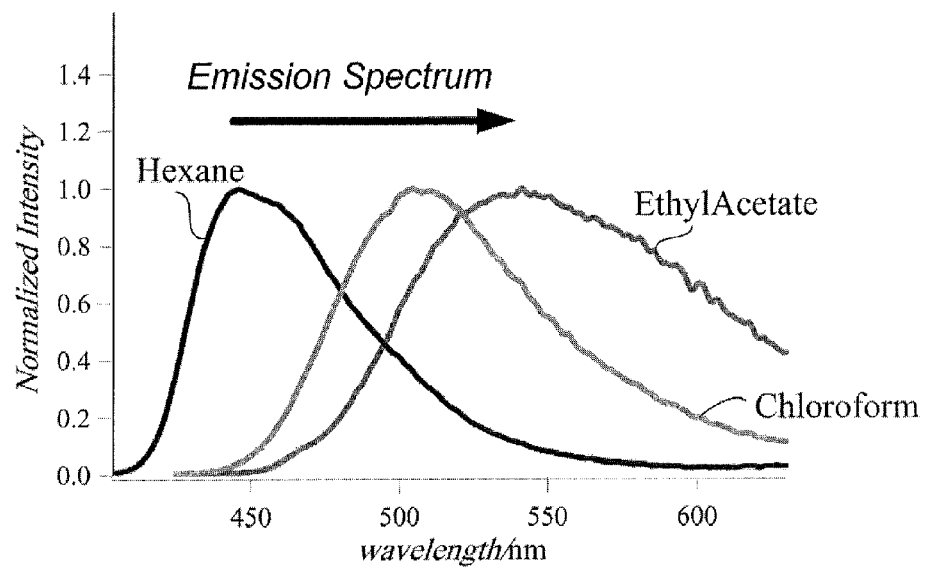
FIG. 2 shows the emission spectra of the quinoline compound of the invention (compound 4) in a hexane solution, a chloroform solution and an ethyl acetate solution.

As obvious from the data in Table 1, the luminescence behavior in FIG. 1 and the emission spectra in FIG. 2, the compound 4 exhibited significant solvatochromism (solvent-dependent emission color change).

As for the compound 4, fluorescence spectrometry was performed using the green-emitting crystal (G-type) and the blue-emitting crystal (B-type) formed depending on the difference in the recrystallization condition. About 1 mg of the sample was sandwiched between quartz plates each having a thickness of 1 mm, and analyzed at an excitation wavelength of 390 nm.

The results are shown in Table 2 below; the luminescence behavior is in FIG. 3; and the emission spectra are in FIG. 4.

TABLE 2

|        | $\lambda_{max}$ (nm) | $\lambda_{fmax}$ (nm) | Φ    |
|--------|----------------------|-----------------------|------|
| hexane | 392                  | 446                   | 0.33 |
| G-type | 416                  | 511                   | 0.13 |
| B-type | 416                  | 478                   | 0.26 |

Figure 3:
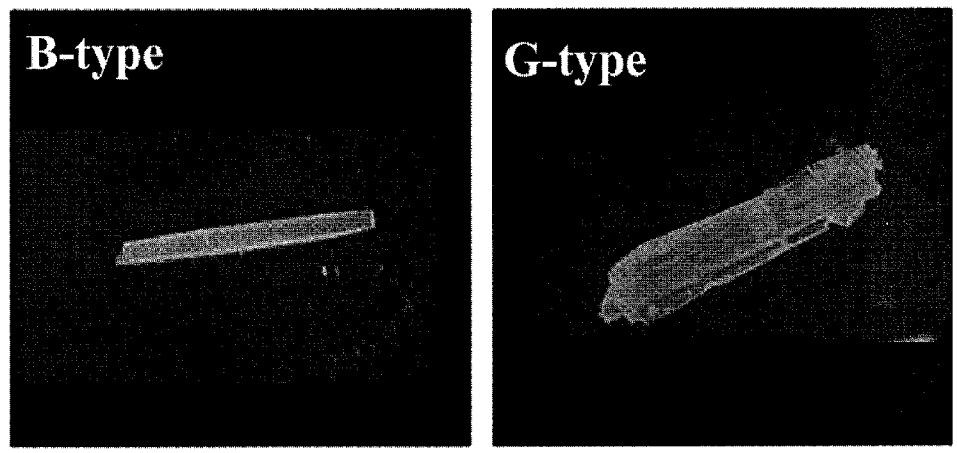
FIG. 3 shows the solid luminescence behavior of B-type and G-type of the quinoline compound of the invention (compound 4).
Figure 4:
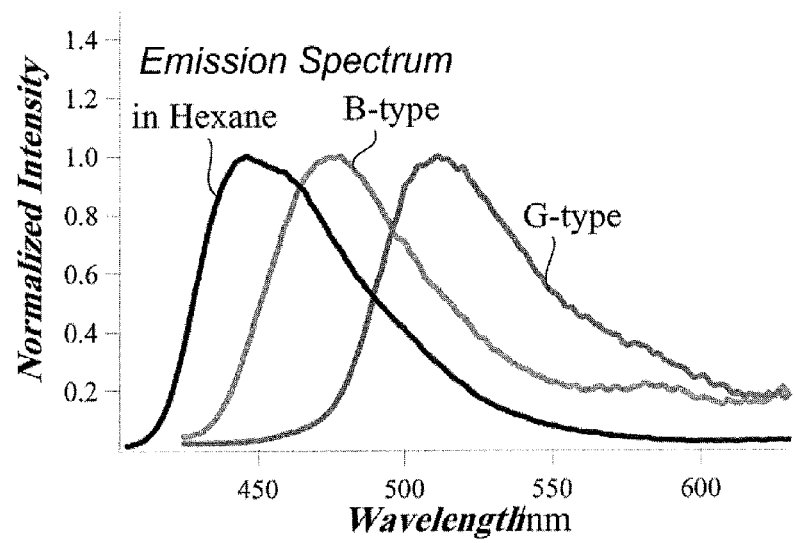
FIG. 4 shows the solution emission spectrum of the quinoline compound of the invention (compound 4) in a hexane solution, and the solid emission spectra of B-type and G-type of the compound.

As obvious from the data in Table 2 and FIGS. 3 and 4, two types of crystals (G-type, B-type) each giving a different luminescent color while being the same molecules were obtained as a result of changing the organic solvent for crystallization of the compound 4, and the color emission from each type of crystal had a sufficient intensity.

Next, 2,4-trifluoromethyl-7-carbazoylquinoline (compound 6) was analyzed. A sample of the compound adjusted to concentration of 10 μM was put into a cuvette of 1 cm×1 cm×2 cm, and analyzed in a hexane, chloroform, ethyl acetate and dimethylsulfoxide solution, using Perkin Elmer's LS50B. The excitation wavelength was 390 nm.

Figure 5:
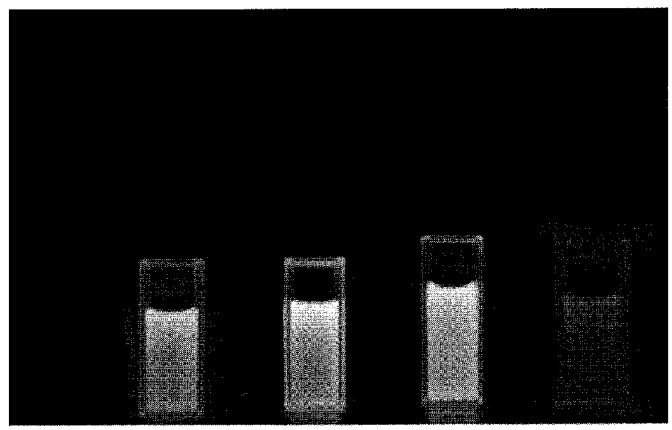
FIG. 5 shows the luminescence behavior of a quinoline compound of the invention (compound 6) in a hexane solution, a chloroform solution, an ethyl acetate solution and a dimethylsulfoxide solution.
Figure 6:
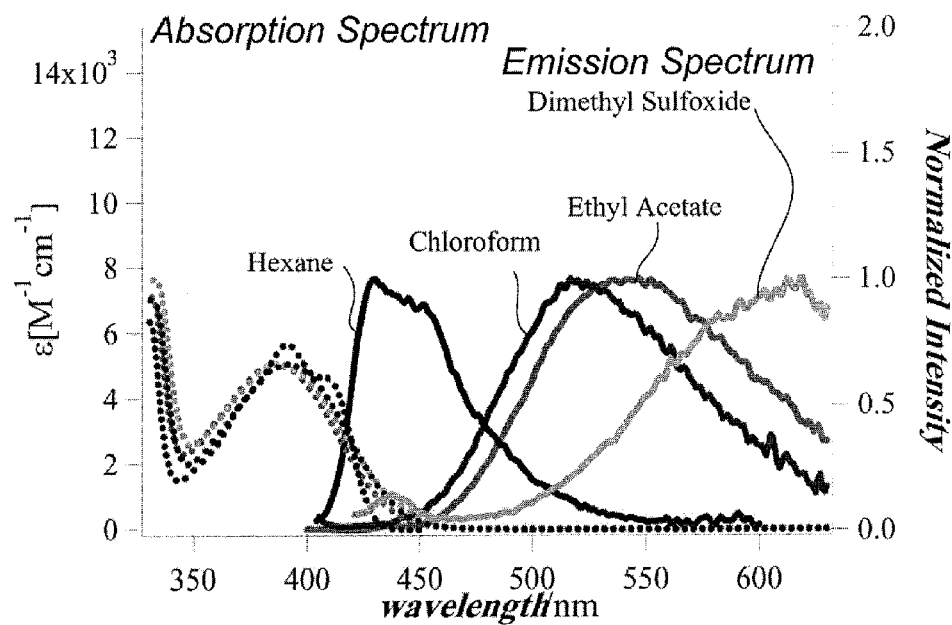
FIG. 6 shows the emission spectra (right axis) of the quinoline compound of the invention (compound 6) in a solution state and the absorption spectrum (left axis) thereof.

FIG. 5 shows the luminescence behavior, and FIG. 6 shows the emission spectra. As obvious from the emission spectra shown in the drawing, the compound 6 exhibited greater solvatochromism in a range of from blue to orange, than the phenyl body of the compound 4.

Next, the crystal of the compound 6 was pounded in a mortar for about 10 minutes. Before and after the pounding pressure application thereto, about 1 mg of the solid sample (before pressure application, after pressure application) was sandwiched between quartz plates each having a thickness of 1 mm, and analyzed at an excitation wavelength of 390 nm.

FIG. 7 shows the emission spectra. As obvious from the emission spectra in the drawing, the luminescent color changed after pressure application to the crystal; and after heated with steaming, the crystal was restored to its original state to emit its original color. Reversible fluorescent piezochromism was confirmed in the compound 6. FIG. 8 includes photographic pictures showing the change of the luminescence behavior.

INDUSTRIAL APPLICATION FIELDS

The quinoline compound of the invention can emit light in a crystal state, and its luminescent color may change not requiring modification of molecular configuration. The compound enables reversible luminescent color change in response to external pressure such as heat and pressure. The compound is therefore useful in light-emitting devices, etc., and its industrial applicability is great.

What is claimed is:

1. A solid luminescent quinoline compound represented by the following general formula (1):

[Formula 1]

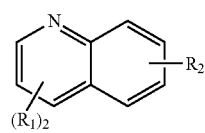

wherein $R_1$ may be the same or different, each representing any of $CF_3$ or $CF_3CF_2$; $R_2$ represents an amino group, an N,N-dimethylamino group, an N-phenylamino group, a carbazole group, an N-methylamino group or an N-methyl-N-phenylamino group.

2. The solid luminescent quinoline compound according to claim 1, represented by the following chemical formula (1-1):

[Formula 2]

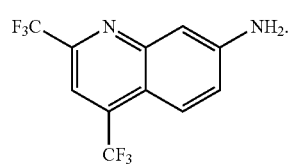

3. The solid luminescent quinoline compound according to claim 1, represented by the following chemical formula (1-2):

[Formula 3]

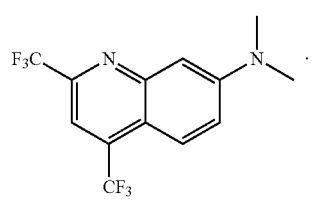

4. The solid luminescent quinoline compound according to claim 1, represented by the following chemical formula (1-3):

[Formula 4]

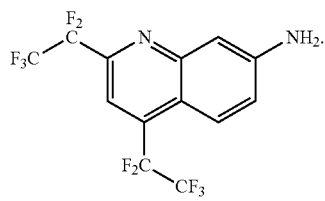

5. The solid luminescent quinoline compound according to claim 1, represented by the following chemical formula (1-4):

[Formula 5]

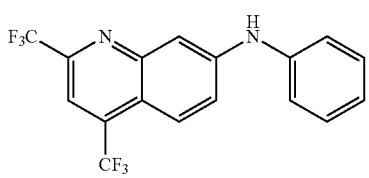

6. A solid luminescent quinoline compound represented by the following chemical formula (1-5):
[Formula 6]
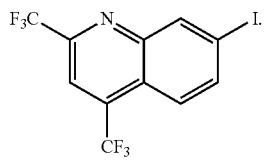
(1-5)
7. The solid luminescent quinoline compound according to claim 1, represented by the following chemical formula (1-6):
[Formula 7]
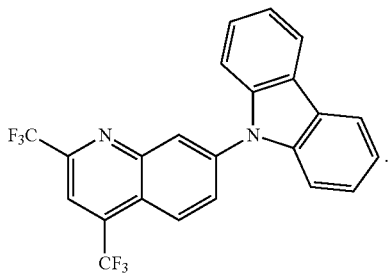
(1-6)